United States Patent
Cemic et al.

(10) Patent No.: US 7,271,889 B2
(45) Date of Patent: Sep. 18, 2007

(54) DEVICE AND METHOD FOR INSPECTING AN OBJECT

(75) Inventors: Franz Cemic, Weilmünster (DE); Lambert Danner, Wetzlar-Naunheim (DE); Uwe Graf, Solms (DE); Robert Mainberger, Braunfels (DE); Dirk Sönksen, Schöffengrund (DE); Volker Knorz, Hüttenberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 416 days.

(21) Appl. No.: 10/524,687

(22) PCT Filed: Aug. 21, 2003

(86) PCT No.: PCT/EP03/09274

§ 371 (c)(1),
(2), (4) Date: Feb. 15, 2005

(87) PCT Pub. No.: WO2004/019108

PCT Pub. Date: Mar. 4, 2004

(65) Prior Publication Data

US 2005/0259245 A1    Nov. 24, 2005

(30) Foreign Application Priority Data

Aug. 23, 2002 (DE) .................. 102 39 548

(51) Int. Cl.
*G01N 21/00* (2006.01)
*G01N 21/55* (2006.01)
(52) U.S. Cl. .................. 356/237.2; 356/445
(58) Field of Classification Search ........... 356/237.2, 356/399–401

See application file for complete search history.

(56) References Cited

U.S. PATENT DOCUMENTS

| 1,943,510 | A | * | 1/1934 | Bauersfeld et al. ......... 359/387 |
| 3,930,713 | A | | 1/1976 | Stankewitz et al. |
| 4,127,318 | A | * | 11/1978 | Determann et al. ......... 359/387 |
| 4,881,802 | A | | 11/1989 | Stankewitz |
| 5,138,176 | A | * | 8/1992 | Nishi ....................... 250/548 |

(Continued)

FOREIGN PATENT DOCUMENTS

DE         2 021 784        11/1970

(Continued)

*Primary Examiner*—Gregory J. Toatley, Jr.
*Assistant Examiner*—Jarreas Underwood
(74) *Attorney, Agent, or Firm*—Foley & Lardner LLP (57) ABSTRACT

A device and method for inspecting an object (2) uses a bright field illumination beam path (4) of a bright field light source (5), said beam path being formed so that it passes through the projection optics (3), and a dark field illumination beam path (6) of a dark field light source (7), this beam path being formed so that it also passes through the projection optics (3). The object (2) can be projected by the projection optics (3) onto the least one detector (8), and the object (2) is simultaneously illuminated by both light sources (5, 7). In order to simultaneously detect bright field images and dark field images without involving complicated filtering operations, the light used for the dark field illumination is pulsed and the pulse intensity of the light used for the dark field illumination is greater by at least one order of magnitude than the intensity of the continuous light, which is used for the bright field illumination, during a pulsed interval.

17 Claims, 4 Drawing Sheets

U.S. PATENT DOCUMENTS

| | | |
|---|---|---|
| 5,461,474 A | 10/1995 | Yoshii et al. |
| 5,917,588 A * | 6/1999 | Addiego ................. 356/237.2 |
| 6,061,125 A * | 5/2000 | Thomas et al. ......... 356/237.1 |
| 6,075,883 A | 6/2000 | Stern et al. |
| RE36,799 E * | 8/2000 | Nishi ......................... 250/548 |
| 6,122,046 A * | 9/2000 | Almogy ................... 356/237.2 |
| 6,153,873 A * | 11/2000 | Wolf ....................... 250/208.1 |
| 6,198,529 B1 * | 3/2001 | Clark et al. ............. 356/237.5 |
| 6,246,788 B1 | 6/2001 | Pattikonda et al. |
| 6,248,988 B1 * | 6/2001 | Krantz ................... 250/201.3 |
| 6,603,874 B1 * | 8/2003 | Stern et al. ................ 382/144 |
| 6,633,375 B1 | 10/2003 | Veith et al. |
| 6,661,912 B1 * | 12/2003 | Taguchi et al. ............ 382/145 |
| 6,801,315 B2 * | 10/2004 | Finarov et al. ............ 356/401 |
| 6,818,459 B2 * | 11/2004 | Wack et al. ................. 438/14 |
| 6,891,610 B2 * | 5/2005 | Nikoonahad et al. .... 356/237.2 |
| 6,891,627 B1 * | 5/2005 | Levy et al. ................. 356/625 |
| 6,922,236 B2 * | 7/2005 | Vaez-Iravani et al. ... 356/237.2 |
| 7,061,600 B2 * | 6/2006 | Maeda et al. ............ 356/237.2 |
| 7,106,425 B1 * | 9/2006 | Bultman et al. ............... 356/73 |
| 7,136,159 B2 * | 11/2006 | Tsai et al. ................ 356/237.5 |
| 2002/0102749 A1 * | 8/2002 | Fielden et al. ................ 438/14 |
| 2002/0109843 A1 * | 8/2002 | Ehsani et al. ............... 356/400 |

FOREIGN PATENT DOCUMENTS

| | | |
|---|---|---|
| DE | 23 31 750 A1 | 1/1975 |
| DE | 37 14 830 A1 | 11/1988 |
| DE | 199 03 486 A1 | 8/2003 |
| EP | 0 183 946 B1 | 3/1989 |
| WO | WO 00/10114 A1 | 2/2000 |
| WO | WO 02/01193 A2 | 1/2002 |

* cited by examiner

DEVICE AND METHOD FOR INSPECTING AN OBJECT

The present invention relates to a device and a method for inspecting an object, having a bright field illumination beam path of a bright field light source formed with respect to an imaging optical arrangement, having a dark field illumination beam path of a dark field light source formed with respect to the imaging optical arrangement, the object being imaged onto at least one detector by means of the imaging optical arrangement and the object being illuminated simultaneously by the two light sources.

Apparatuses of the generic type have been known for some time. In optical inspection technology, in particular, complex structures on planar substrates are inspected image field by image field. This is the case primarily in the semiconductor industry for optically examining patterned surfaces of masks and wafers. In this case, defects that are present, by way of example, are intended to be detected or classified. Examples of defects that occur may be grains of dust, blisters in the resist, resist residues on wafers, chipping of edges or scratches.

A microscope with Köhler bright field illumination, by way of example, may serve as the device. Thus, a bright field illumination is formed by the Köhler illumination with regard to the microscope objective—that is to say the imaging optical arrangement and, if appropriate, the effective detector area. A dark field illumination can be realized in a known manner in the case of a microscope, for example by using a dark field microscope objective. In the case of such an objective, the light serving for the dark field illumination is guided between the imaging optical arrangement for the bright field imaging and an objective housing formed in mirrored fashion in such a way that it impinges on the object in an angular range or aperture range that lies outside the numerical aperture of the imaging optical arrangement for the bright field imaging. In order to define the bright field or dark field illumination beam path, it is necessary, if appropriate, to take account of the effective detection area of the detector or the entire detection beam path running between object and detector, in particular when the aperture ranges of the bright field and dark field illumination beam paths virtually adjoin one another.

Experience shows that detection of elevated and recessed structures by means of bright field illumination alone is not possible or is possible only to a limited extent. For this reason, a transition has been made to carrying out an additional inspection, which is effected with the aid of a dark field illumination provided in the device. This type of illumination is particularly suitable for the detection of elevated and recessed structures, which structures may be defective structures. Planar structures remain invisible in the case of dark field illumination. In contradistinction, elevated structures appear with high contrast as bright lines on a dark background. Irregularities in these lines indicate possible defects.

DE 199 03 486 A1 discloses a method for simultaneous bright field and dark field illumination in the case of which at least one of the two beam bundles is encoded by means of the color—i.e. the wavelength of the light—, the polarization or the modulation, i.e. amplitude or frequency modulation. The bright field image is separated from the dark field image by means of corresponding filters or detector devices.

Furthermore, DT 2 021 784, DE 23 31 750 C3 and DE 37 14 830 A1 disclose illumination devices for microscopes in the case of which a changeover can optionally be made between bright field and dark field illumination. Simultaneous bright field/dark field illumination is not provided in this case.

EP 0 183 946 B1 discloses combined bright field and dark field illumination with two light sources in the case of which a changeover is made from bright field to dark field illumination by means of mechanical closures (shutters) that are respectively assigned to a light source. In this case, it is also provided that both types of illumination are used simultaneously, that is to say both shutters are opened. In this mode, however, the radiation of the bright field image surpasses that of the dark field image, so that simultaneous detection of an object with both illumination modes is not possible.

Consequently, the illumination systems disclosed in the prior art are either not suitable for simultaneous bright field and dark field illumination, or a simultaneous illumination in both modes is indeed possible, but the images thus obtained are unusable or can only be separated from one another with increased complexity.

Therefore, the present invention is based on the object of specifying and developing a device and a method for inspecting an object in such a way that a simultaneous detection of bright field and dark field images is possible, the intention being to dispense with complex filter operations.

The device according to the invention for inspecting an object achieves the above object by means of the features of patent claim 1. Accordingly, such a device is characterized in that the light serving for dark field illumination is pulsed, and in that the pulse intensity of the light serving for dark field illumination is at least one order of magnitude greater than the intensity—relative to a pulse interval—of the continuous light serving for bright field illumination.

According to the invention, it has firstly been recognized that the luminous efficiency differs greatly in the case of a bright field illumination and a dark field illumination. Thus, almost exclusively the light reflected at the object is detected in the case of a bright field illumination, whereas almost exclusively the light scattered at the object is detected in the case of a dark field illumination. Consequently, the intensity ratios differ greatly in the case of a simultaneous detection, for example 100:1 or 1000:1. Therefore, in the manner according to the invention, the pulse intensity of the light serving for dark field illumination is chosen to be at least one order of magnitude greater than the intensity—relative to a pulse interval—of the continuous light serving for bright field illumination, to be precise relative to the intensity ratios of the light of the two light sources at the object or in the object plane of the imaging system. As a result of this, in a particularly advantageous manner, the intensity of the light scattered at the object by the dark field illumination is comparable with or at least of the same order of magnitude as the intensity of the light reflected at the object by the bright field illumination, so that it is not necessary to make elevated requirements of the properties—e.g. the dynamic range—of one or more detectors.

In a further manner according to the invention, the light serving for dark field illumination is pulsed. Consequently, strictly speaking, a simultaneous illumination by the two light sources is afforded only when the pulsed light of the dark field light source illuminates the object. This means, however, in an especially advantageous manner, that it is not necessary to provide shutters in the illumination beam paths since either only a bright field illumination or a simultaneous bright field and dark field illumination is present, as it were continuously. In this respect, object image data can be detected continuously by means of the detector or by means of a detector system having a detector, in which case, in accordance with the temporal sequence of the illumination conditions, only bright field images of the object and bright field images together with dark field images of the object can be detected and evaluated. In principle, the pulse repetition frequency of the dark field light source can be adapted to the read-out characteristic of the detector.

The dark field light source used may be a light source whose light power to be provided, relative to continuous operation, does not have to be 10 or 1000 times as high as that of the continuously operated light source for bright field illumination. The light power to be provided by the dark field light source relates to the power of the individual pulses. According to the invention, this light power is to be chosen to be at least one order of magnitude greater than the intensity—relative to a pulse interval—of the continuous light serving for bright field illumination. It is only by virtue of this high intensity of the dark field light pulses that the dark field image of the object, with simultaneous bright field illumination, can be detected without additional filters or similarly separating detection devices, but rather directly from the recorded image. In contradistinction thereto, the previously known devices always required additional filters, demodulation means, etc. in order to separate the dark field image from the bright field image. Suitable light sources that can be used as dark field light sources are advantageously commercially available in a large selection and in some instances inexpensively. Thus, by way of example, it is possible to use a Xenon flash lamp, a laser or an LED as dark field light sources.

In concrete terms, the pulse intensity of the light serving for dark field illumination is 10 to 10 000 times greater than the intensity—relative to a pulse interval—of the continuous light serving for bright field illumination. Since, in particular, the intensity of the light scattered at the object depends on the object property or on the property of the object surface, the intensity ratio of the two light sources can be chosen in a manner dependent on the object to be inspected, in particular on the type of objects to be inspected, e.g. for masks for the semiconductor industry. Ultimately, the intensity of the continuously operating bright field light source for bright field illumination will be chosen in such a way that an optimum contrast can be obtained with the detector or with the detector system in this case. The intensity of the pulsed dark field light source is then chosen in such a way that an optimum contrast can likewise be obtained in the case of the dark field illumination, and that both the image data detected in the different illumination modes have an optimum intensity ratio relative to one another.

In one possible embodiment of the device, the dark field light source emits pulsed light. What is involved in this case is a light source that only operates in pulsed operation. As an alternative, it may also be provided that the dark field light source emits continuous light, or that a partial beam of the bright field light source for the bright field illumination is coupled out for the dark field illumination beam path. The continuous light is then subdivided into individual pulses by means of at least one optical component. This optical component may be a shutter, a rotating shutter wheel, an electro-optical or an acoustic-optical modulator, the optical component being arranged in the dark field illumination beam path.

In an especially preferred embodiment, the read-out and/or evaluation readiness of the detector and/or of the detection system is synchronized with the pulse sequence of the light serving for dark field illumination. This measure makes it possible, on the one hand, to adapt the properties of the detector and/or of the detection system to the illumination conditions currently prevailing, so that, in an advantageous manner, an overdriving of the detector, by way of example, can be prevented to a greater extent. On the other hand, this measure enables the image data of the respective illumination mode to be assigned to the individual illumination modes with the aid of the detection system and/or an evaluation system connected downstream of the detection system, so that a targeted evaluation of image data can be effected which takes account of the respective characteristics of the detected images.

In concrete terms, the synchronization may be effected on the basis of a pulse sequence signal of the dark field light source or on the basis of a control signal of the optical component. If the pulsed dark field light source has a trigger output that outputs a corresponding trigger signal if a light pulse is emitted, this signal can be utilized for synchronization of the detector or the detection system. As an alternative to this, it would be possible, by way of example, to effect synchronization by detection of the pulse sequence of the dark field light source on the basis of a partial beam which is extracted from the dark field light source and is conducted onto a photodiode. The output signal of said photodiode can then be used for synchronization. If a continuously operating light source is used as the dark field light source, and this light is subdivided into individual pulses by means of an optical component, then the control signal of the optical component may serve as synchronization signal for the detector and/or for the detection system. Furthermore, a delay circuit that can be used to compensate for electronic propagation time differences or temporal offsets, by way of example, may be provided for synchronization purposes.

In a preferred embodiment, the optical axis of the bright field illumination beam path is essentially perpendicular to the surface of the object to be inspected or is essentially perpendicular to the object plane of the imaging optical arrangement. This condition is met in the case of an inspection system designed in the form of a microscope, by way of example, by virtue of the microscope having a Köhler illumination system, since, in this case, the optical axis of the bright field illumination beam path is essentially perpendicular to the object plane of the imaging optical arrangement. If the inspection system is to be used to inspect objects with essentially planar surface structures—thus for example wafers or masks for the semiconductor industry—, the object to be inspected will expediently be oriented and/or positioned in such a way that its surface is arranged perpendicular to the optical axis of the bright field illumination beam path. In the inspection of at least partly transparent masks for the semiconductor industry, a bright field illumination in the transmitted light mode is also conceivable, the optical axis of the bright field illumination beam path then likewise being essentially perpendicular to the surface of the object to be inspected.

In another embodiment, the optical axis of a detection beam path running between object and detector is essentially perpendicular to the surface of the object to be inspected. In this respect, an arrangement of the detection beam path as is present in a conventional microscope, by way of example, may be involved in this case. The bright field illumination beam path may thus overlap or run coaxially with the detection beam path in regions.

The optical axis of the dark field illumination beam path may be arranged, at least in regions, coaxially with the optical axis of the bright field illumination beam path and/or coaxially with the optical axis of the detection beam path. This is the case in particular when a dark field objective is used in the case of an inspection apparatus designed as a microscope, in which case the illumination beam paths of the two light sources may be arranged in a similar manner to that known for example from EP 0 183 946 B1.

In a preferred embodiment, the optical axis of the dark field illumination beam path has an angle of between 5 and 90 degrees with respect to the optical axis of the bright field illumination beam path and/or with respect to the optical axis of the detection beam path. What is involved in this case is, by way of example, an arrangement as known from FIG. 5 from DE 199 03 486 A1, the dark field illumination beam path thus being led past the microscope objective on the object side, as it were. In this case, in an especially advantageous manner, the angle between the optical axis of the dark field illumination beam path and the optical axis of the bright field illumination beam path may be set in such a way as to obtain optimum results in the detection of the images which are recorded by means of the dark field illumination. Consequently, the angle setting may have to be varied in a manner dependent on the object structures to be detected. This can be achieved for example by means of the optical components of the dark field illumination beam path; if appropriate, it is also possible to vary the illumination aperture of the dark field illumination and thus to effect a further adaptation to the object structures to be detected.

In principle, it is conceivable for the light of the bright field light source and/or of the dark field light source to have a coding. In this case, the technology disclosed in DE 199 03 486 A1 is combined with the device according to the invention. As a result of this, advantages may be afforded, under certain circumstances, in the image data evaluation if, by way of example, the pulsed light of the dark field light source has a wavelength of 488 nm, the light of the bright field light source has a wavelength of 365 nm and the detector comprises a color CCD camera. The detected image data can then be assigned to the respective illumination mode during the data evaluation solely with regard to the color information. Quite generally, the coding may be formed by the polarization, amplitude modulation, frequency modulation, pulse frequency modulation and/or by the selection of a wavelength or a wavelength range.

The bright field light source used may be a white light source, preferably a DC lamp. Xenon, mercury-vapor high-pressure lamps or other arc lamps in DC operation are usually used for inspection devices for inspecting wafers and masks for the semiconductor industry, corresponding color filters or reflection filters being able to filter out all wavelengths apart from a wavelength of the emission spectrum of the light source, which is then used for the object illumination. Lasers or LEDs (Light-Emitting Diode) that emit continuous light are likewise conceivable.

The dark field light source may be designed as a Xenon flash lamp, a laser or an LED or LED arrangement, the dark field light source emitting pulsed light. The pulse durations of the pulses of the dark field light source to be used usually lie in a range of 1 ms to 0.01 ms, but are preferably 0.1 ms. The pulse power of the individual pulses is typically of the order of magnitude of 1 watt in this case.

In a preferred embodiment, the detector comprises a CCD camera, it being possible to use a monochrome and/or a color CCD camera. The spatial resolution is generally higher in the case of a monochrome CCD camera than in the case of a color CCD camera. A monochrome CCD camera is preferably used particularly in the case of inspection devices and in the case of coordinate measuring devices for inspecting or measuring coordinates of wafers and masks in the semiconductor industry, where a high spatial resolution is demanded. The CCD camera control, in particular, can be synchronized with the pulse sequence signal of the dark field light source with regard to the detection or read-out behavior of the CCD camera.

In principle, the device according to the invention is coupled to a control computer. Usually, said control computer not only controls automatic image data recording of a plurality of objects that are to be inspected automatically, but also has a storage unit on which the detected object data or extracted measurement results are stored and/or evaluated.

In respect of the method, the object mentioned in the introduction is achieved by means of the features of the coordinate patent claim 17. Accordingly, in the method for inspecting an object, the object is illuminated simultaneously with a bright field light source for bright field illumination, on the one hand, and with a dark field light source for dark field illumination, on the other hand, and the object is imaged onto at least one detector by means of an imaging optical arrangement. The method according to the invention for inspecting an object is characterized in that the light serving for dark field illumination is pulsed, the pulse intensity of the light serving for dark field illumination being at least one order of magnitude greater than the intensity—relative to a pulse interval—of the continuous light serving for bright field illumination.

The method according to the invention is preferably used for operating a device according to one of patent claims 1 to 16. In order to avoid repetition, reference is made in this regard to the preceding part of the description.

It is especially preferred for the object inspection to be effected automatically. Thus, a program according to which different predetermined regions of the object are detected may be executed on a control computer assigned to the device. For this purpose, the device may be coupled to a positioning system that positions the object relative to the imaging optical arrangement and is preferably likewise driven by the control computer. It is furthermore conceivable for a plurality of objects to be automatically fed to the device—for example by means of a loading robot—and to be detected fully automatically object by object in each case in regions. The control computer may furthermore comprise a program module which makes it possible to evaluate the detected image data with regard to possible defects of the respective object. Methods of digital image processing may generally be used in this case, it being possible to provide a comparison of the detected object regions with a known calibration object. For documentation or logging of the defects identified, the corresponding image regions of the respective object or merely their coordinates may be stored on the storage unit of the control computer.

There are now various possibilities for configuring and developing the teaching of the present invention in an advantageous manner. In this respect, reference should be made, on the one hand, to the patent claims that are subordinate to patent claims 1 and 17 and, on the other hand, to the following explanation of the preferred exemplary embodiments of the invention with reference to the drawing. Generally preferred configurations and developments of the teaching are also explained in conjunction with the explanation of the preferred exemplary embodiments of the invention with reference to the drawing, in which:

Figure 1:
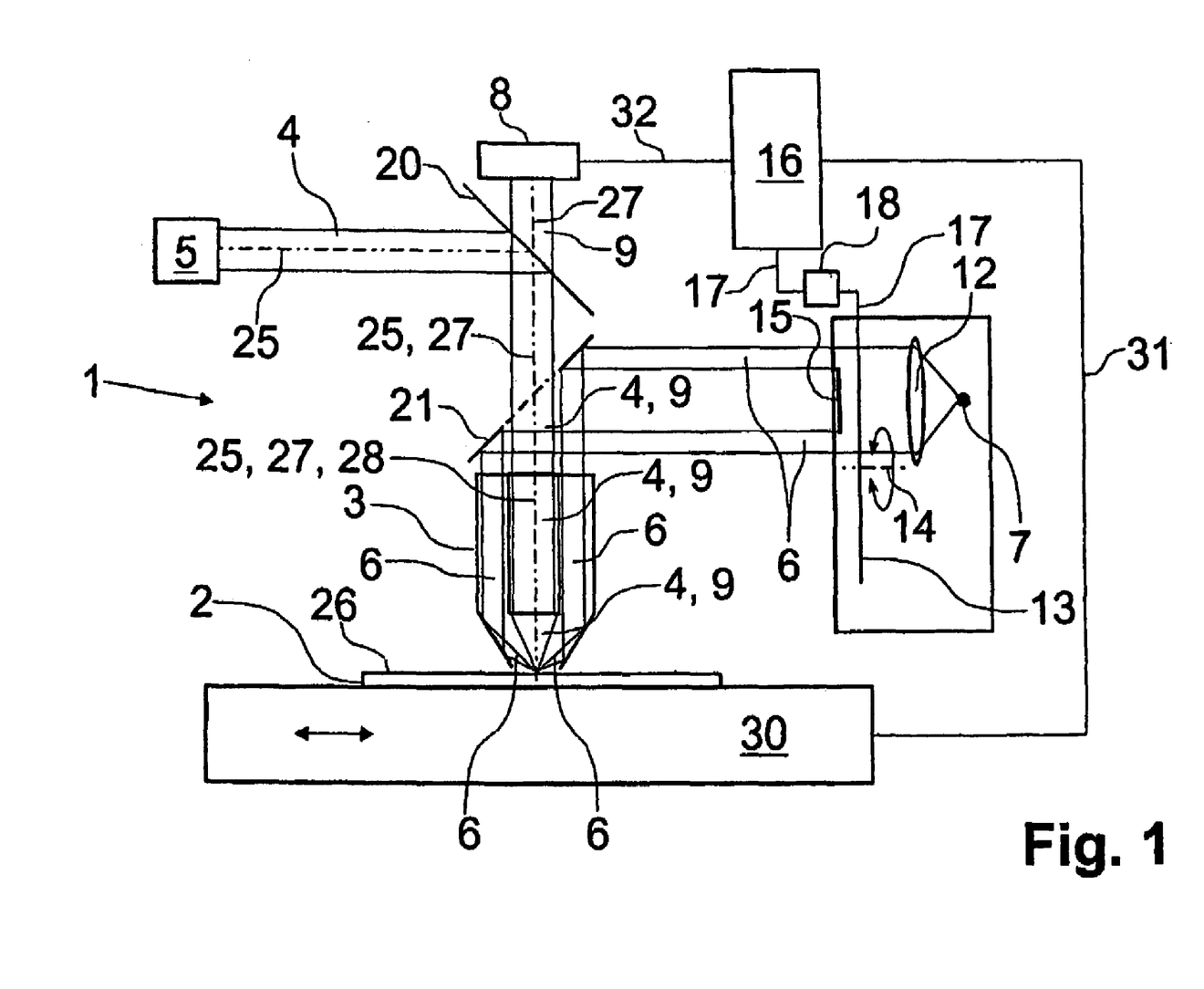
FIG. 1 shows a schematic illustration of a first exemplary embodiment of a device according to the invention.
Figure 2:
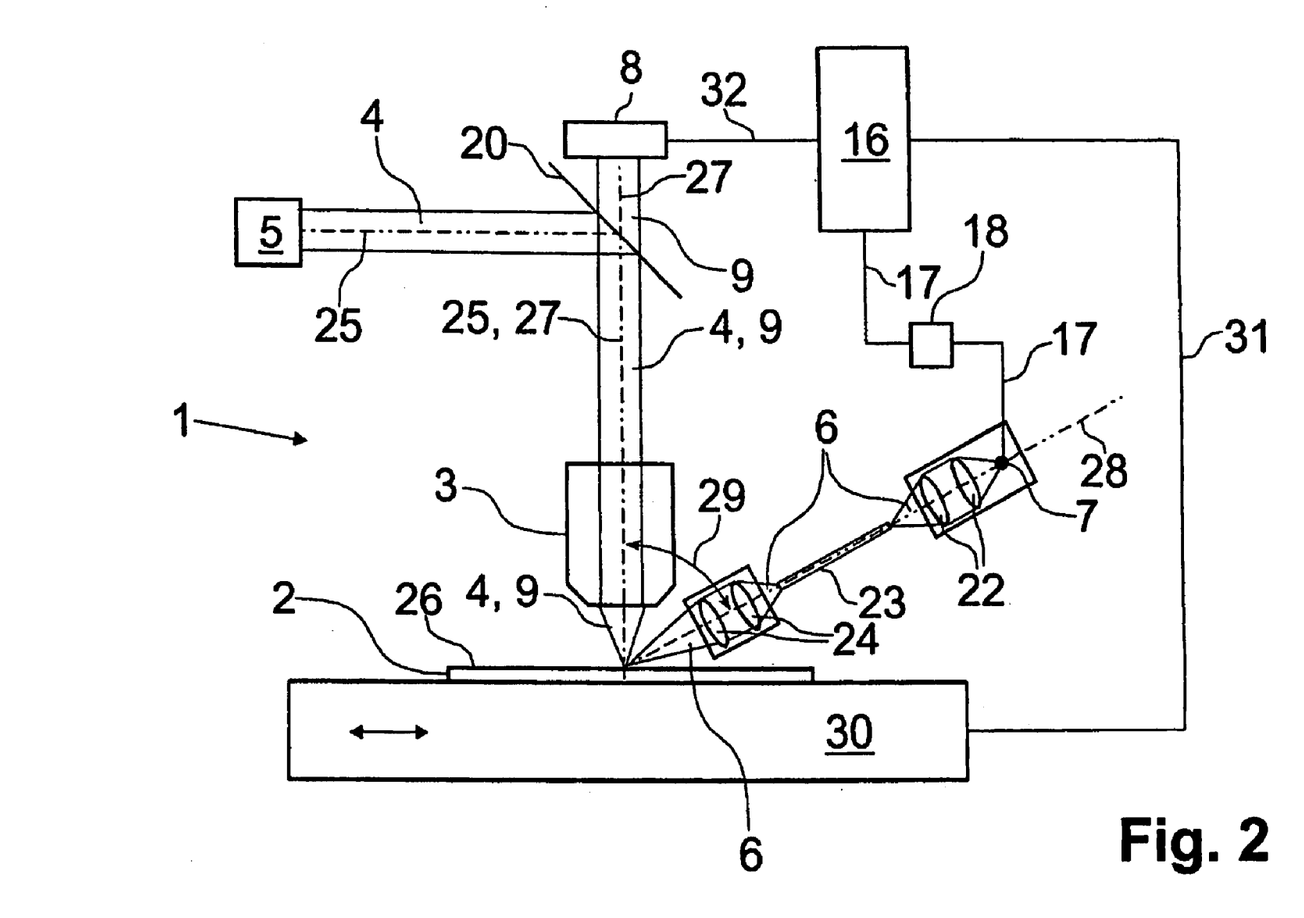
FIG. 2 shows a schematic illustration of a second exemplary embodiment of a device according to the invention.

FIGS. 1 and 2 show schematic illustrations of a device 1 for inspecting an object 2. Said device 1 is an optical inspection device by means of which masks and wafers for the semiconductor industry can be examined in particular for defects. The device 1 has a bright field illumination beam path 4 of a bright field light source 5 formed with respect to an imaging optical arrangement 3. Furthermore, a dark field illumination beam path 6 of a dark field light source 7 is provided with respect to the imaging optical arrangement 3. The object 2 is imaged into a detector 8 by means of the imaging optical arrangement 3, the detection beam path 9 running from the object 2 to the detector 8. The object 2 is illuminated simultaneously by the two light sources 5 and 7.

Figure 3A:
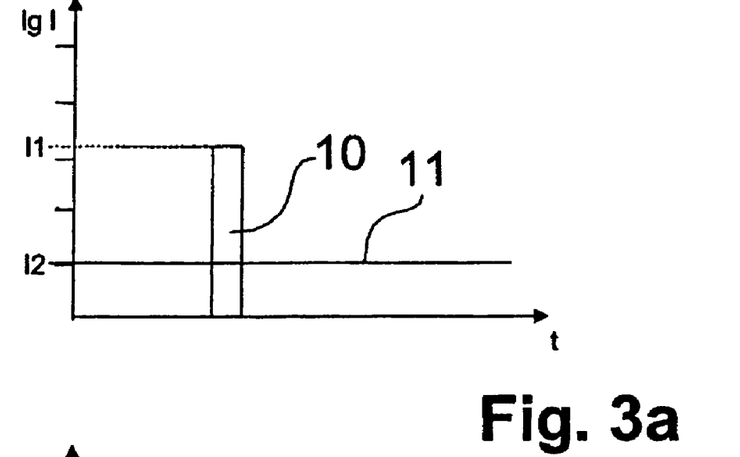
FIG. 3a shows a schematic illustration of a diagram of the temporal profile of the light intensities of the illumination light of the bright field light source and of the dark field light source at the location of the object in the case of the exemplary embodiment from FIG. 2.

According to the invention, the light of the dark field light source 7 serving for dark field illumination is pulsed. FIG. 3a shows a schematic diagram of the logarithm of the light intensities of the two light sources 5 and 7 (lg I) in arbitrary units as a function of time t. In this case, the temporal intensity profile relates to the illumination intensity profile of the light of the two light sources 5 and 7 that is present at the object 2. For the sake of simplicity, the temporal intensity profile 10 of only one light pulse of the dark field light source 7 is shown. The temporal intensity profile of the bright field light source 5 is shown by means of the reference symbol 11. The bright field light source 5 emits continuous light having a constant intensity. The diagram of FIG. 3a shows that the pulse intensity I1 of the light serving for dark field illumination is approximately two orders of magnitude greater than the intensity I2—relative to the pulse interval—of the continuous light serving for bright field illumination. Consequently, the pulse intensity I1 of the light serving for dark field illumination, in this exemplary embodiment, is approximately 100 times greater than the intensity I2—relative to a pulse interval—of the continuous light serving for bright field illumination. This has the advantage that the dark field image can be separated from the bright field image without additional auxiliary means, such as e.g. filters, since it appears brighter than the bright field image itself directly on the detector 8.

Figure 3B:
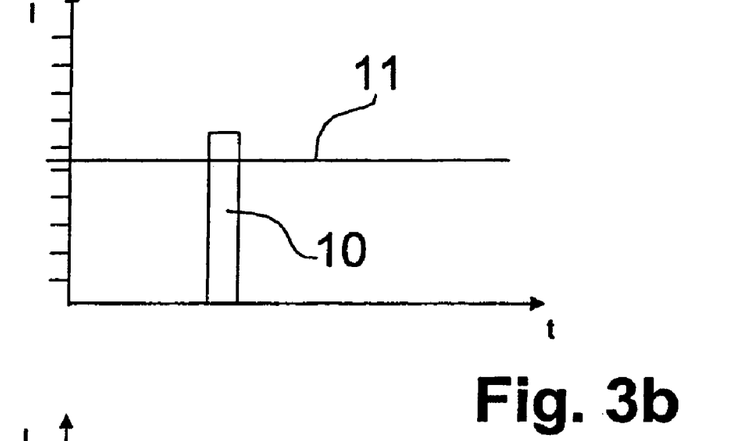
FIG. 3b shows a schematic illustration of a diagram of the temporal profile of the light intensities of the light of the bright field light source and of the dark field light source, which light is reflected and scattered at the object, at the location of the detector in the case of the exemplary embodiment from FIG. 2.
Figure 3C:
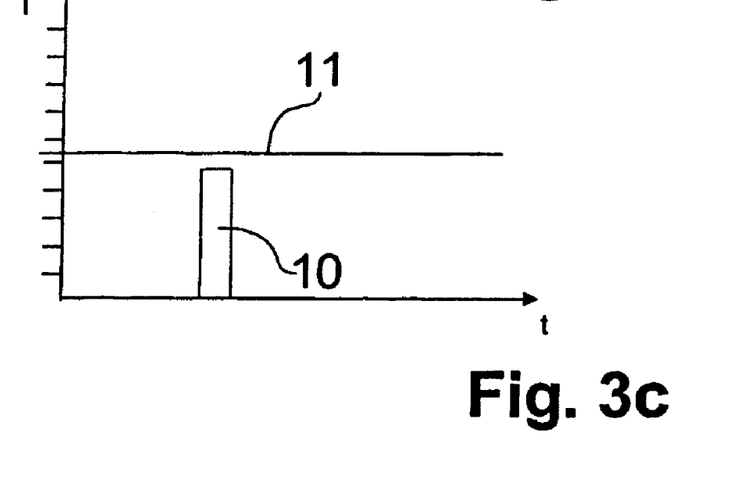
FIG. 3c shows a schematic illustration of a diagram of the temporal profile of the light intensities of the light of the bright field light source and of the dark field light source, which light is reflected and scattered at the object, at the location of the detector in the case of the exemplary embodiment from FIG. 2, a different object having being detected.

The temporal intensity profiles shown in FIGS. 3b and 3c correspond to the light intensity—present at the detector 8—of the light of the bright field light source 5 reflected at the object 2, on the one hand, and of the light of the dark field light source 7 scattered at the object 2, on the other hand. The diagrams of the FIGS. 3b and 3c thus show the light intensities of the light of the two light sources 5 and 7, which light is reflected and scattered at the object, in arbitrary units as a function of time t. In the case of the temporal intensity profile shown in FIG. 3c, the detection is based on a different object than was the case for the detected temporal intensity profile from FIG. 3b. It can be gathered from FIGS. 3b and 3c that the two objects differ with regard to the intensity of the proportion of scattered light at the object surfaces.

The dark field light source 7 shown in FIG. 2 is an arc lamp that emits pulsed light. The dark field light source 7 shown in FIG. 1 is likewise an arc lamp, but one which emits continuous light having a constant intensity. The light of the dark field light source 7 from FIG. 1 is subdivided into individual pulses after collimation by means of a lens 12 with the aid of an optical component 13 designed in the form of a rotating shutter wheel. The shutter wheel rotates about the rotation axis 14 and has light-transmissive regions arranged circumferentially through which the light of the dark field light source 7 can pass. A for example circular region is masked out by the diaphragm 15, so that only an annular illumination cross section is present in the further course of the dark field illumination beam path 6.

The read-out and evaluation readiness of the detector 8 and of the detection system 16 arranged downstream of the detector 8 is synchronized with the pulse sequence of the light of the dark field light source 7 serving for dark field illumination. In FIG. 1, the synchronization line 17 connects the optical component 13 to the detection system 16. In FIG. 2, the synchronization line 17 connects the dark field light source 7 from FIG. 2 to the detection system 16. For synchronization purposes, a trigger signal is made available in each case by the optical component 13 from FIG. 1 and the dark field light source 7 from FIG. 2. The trigger signal of the optical component 13 may be generated by means of a light barrier (not depicted) by way of example. The dark field light source 7 from FIG. 2 generates a trigger signal on the basis of its internal control. The detector 8 is connected to the detection system 16 arranged downstream by means of the control and read-out line 32. For synchronization purposes, a delay circuit 18 is additionally provided whose offset or delay value can be altered in an adjustable manner.

Figure 4:
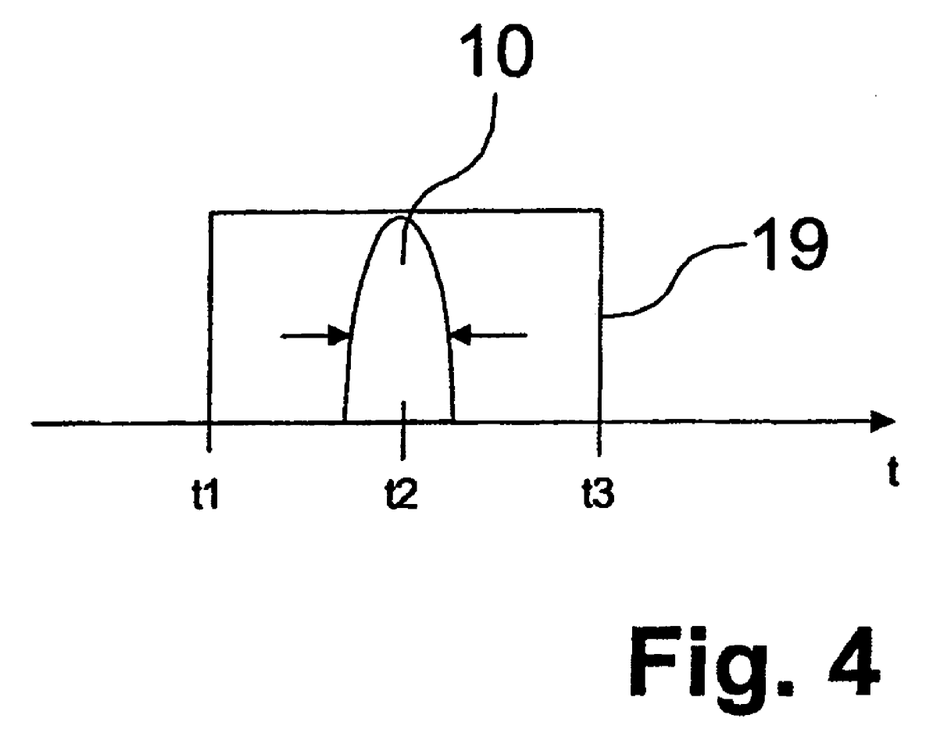
FIG. 4 shows a schematic illustration of a diagram of a temporal profile of a light pulse of the dark field light source and a detection interval of the detector.

FIG. 4 shows a schematic diagram of the temporal intensity profile 10 of a light pulse which has a half value width of less than 0.1 ms indicated by the two arrows. The time interval 19 extending from t1 to t3' identifies the duration in which the detector 8 is in read-out readiness for the light of the dark field light source 7 scattered at the object. In this case, the instant t2 ideally lies centrally between the start and end values t1 and t3 of the time window 19, the instant t2 identifying the center of the light pulse.

The geometrical arrangement of the optical beam paths is discussed below. The bright field illumination beam path 4 in FIGS. 1 and 2 runs from the bright field light source 5 via the beam splitter 20 to the object 2. At the beam splitter 20, the light of the bright field light source 5 is reflected for the most part in the direction of the imaging optical arrangement 3.

The dark field illumination beam path 6 in FIG. 1 runs from the dark field light source 7 firstly to the beam splitter 21, at which the light of the dark field light source 7 is reflected in a mirrored region—shown by solid lines—in the direction of the imaging optical arrangement 3. The illustration shows merely schematically how the light of the dark field light source 7 that is reflected at the beam splitter 21 is guided coaxially outside the bright field illumination beam path 4 in the direction of the object 2, the depiction of a focusing optical arrangement required for this purpose having been dispensed with for the sake of simplicity. The central region of the beam splitter 21 is transparent— depicted in dash-dotted fashion—, so that the light of the bright field light source 5 and the light that is scattered or reflected at the object 2, in the bright field illumination beam path 4 or in the detection beam path 9, can pass through the beam splitter 21 in said region.

The dark field illumination beam path 6 in FIG. 2 runs from the dark field light source 7 to the object 2, to be precise firstly via the coupling-in optical arrangement 22, which couples the light of the dark field light source 7 into the optical waveguide 23. The light emerging from the optical waveguide 23 is focused by means of the focusing optical arrangement 24 into the focal region of the imaging optical arrangement 3 onto the object 2.

It can be gathered from FIGS. 1 and 2 that the optical axis 25 of the bright field illumination beam path 4 between beam splitter 20 and object 2 is perpendicular to the surface 26 of the object 2 to be inspected. At the same time, the optical axis 25 of the bright field illumination beam path 4 is arranged perpendicular to the object plane of the imaging optical arrangement 3, which coincides with the surface 26 of the object 2 facing the imaging optical arrangement 3 and is therefore not depicted separately. The optical axis 27 of the detection beam path 9 running between object 2 and detector 8 is likewise perpendicular to the surface 26 of the object 2 to be inspected and perpendicular to the object plane of the imaging optical arrangement 3.

The optical axis 28 of the dark field illumination beam path 6 in FIG. 1, between beam splitter 21 and object 2, is coaxial with the optical axis 25 of the bright field illumination beam path 4 and coaxial with the optical axis 27 of the detection beam path 9.

FIG. 2 shows that the optical axis 28 of the dark field illumination beam path 6 is at an angle 29—indicated by the arcuate double arrow—with respect to the optical axis 25 of the bright field illumination beam path 4 and with respect to the optical axis 27 of the detection beam path 9.

The bright field light source 5 is a DC lamp. The detector 8 is a CCD camera.

The detection system 16 also comprises a control computer—not depicted separately—which drives the individual components of the device 1. In particular, the object inspection is carried out automatically by means of a program executed on the control computer. For this purpose, the detection system 16 of the device 1 is coupled via a line 31 to a positioning system 30, which is likewise driven by the control computer and positions the object 1. The positioning system 30 positions the object 2 along the direction shown by the double arrow at the positioning system 30 in FIGS. 1 and 2. Furthermore, an object positioning in the two opposite directions perpendicular thereto is provided, that is to say out of the plane of the drawing of FIGS. 1 and 2.

Finally, it should be pointed out that the exemplary embodiments discussed above serve only for describing the claimed teaching, but do not restrict the latter to the exemplary embodiments.

LIST OF REFERENCE SYMBOLS

1 device
2 object
3 imaging optical arrangement
4 bright field illuminating beam path
5 bright field light source
6 dark field illuminating light source
7 dark field light source
8 detector
9 detection beam path
10 temporal intensity profile of a light pulse from (7)
11 temporal intensity profile of the light from (5)
12 lens
13 optical component, rotating shutter wheel
14 rotation axis of (13)
15 diaphram
16 detection system
17 synchronization line
18 delay circuit
19 time interval
20 beam splitter
21 beam splitter
22 coupling-in optical arrangement
23 optical waveguide
24 focusing optical arrangement
25 optical axis of (4)
26 surface to be inspected of (2)
27 optical axis of (9)
28 optical axis of (6)
29 angle between (27) and (28)
30 positioning system
31 line between (16) and (30)
32 control and read-out line
I1 pulse intensity of a light pulse from (7) at the location of the object
I2 intensity of the light from (5) at the location of the object
t1 beginning of the time interval (19)
t2 center of the light pulse
t3 end of the time interval (19)

The invention claimed is:

1. A device for inspecting an object, having a bright field illumination beam path of a bright field light source formed with respect to an imaging optical arrangement, having a dark field illumination beam path of a dark field light source formed with respect to the imaging optical arrangement, the object being imaged onto at least one detector by means of the imaging optical arrangement and the object being illuminated simultaneously by the two light sources characterized in that the light serving for dark field illumination is pulsed, and in that the pulse intensity of the light serving for dark field illumination is at least one order of magnitude greater than the intensity of continuous light serving for bright field illumination;
   wherein the read-out and/or evaluation readiness of the detector and/or of a detection system is synchronized with the pulse sequence of the light serving for dark field illumination.

2. The device as claimed in claim 1, characterized in that the pulse intensity of the light serving for dark field illumination is 10 to 10 000 times greater than the intensity of the continuous light serving for bright field illumination.

3. The device as claimed in claim 1, characterized in that the dark field light source emits pulsed light.

4. The device as claimed in claim 1, characterized in that the dark field light source emits continuous light that can be subdivided into individual pulses by means of at least one optical component.

5. The device as claimed in claim 4 characterized in that the optical component has a shutter, a rotating shutter wheel, an electro-optical or an acoustic-optical modulator.

6. The device as claimed in claim 1, characterized in that a delay circuit is provided for synchronization purposes.

7. The device as claimed in claim 1, characterized in that the optical axis of the bright field illumination beam path is essentially perpendicular to the surface of the object to be inspected or is essentially perpendicular to the object plane of the imaging optical arrangement.

8. The device as claimed in claim 1, characterized in that the optical axis of a detection beam path running between the object and detector is essentially perpendicular to the surface of the object to be inspected or is essentially perpendicular to the object plane of the imaging optical arrangement.

9. The device as claimed in claim 1, characterized in that the optical axis of the dark field illumination beam path, at least in regions, is coaxial with the optical axis of the bright field illumination beam path and/or coaxial with the optical axis of a detection beam path.

10. The device as claimed in claim 1, characterized in that the optical axis of the dark field illumination beam path has an angle of between 5 and 90 degrees with respect to the optical axis of the bright field illumination beam path and/or with respect to the optical axis of a detection beam path.

11. The device as claimed in claim 1, characterized in that the bright field light source is designed as a white light source.

12. The device as claimed in claim 1, characterized in that the dark field light source is designed as a xenon flash lamp, a laser or an LED (Light Emitting Diode) or an LED arrangement.

13. The device as claimed in claim 1, characterized in that the detector is designed as a CCD camera.

14. The device as claimed in claim 1, further comprising a coupling to a control computer.

15. A method for inspecting an object, the object being illuminated simultaneously with a bright field light source for bright field illumination, on the one hand, and with a dark field light source for dark field illumination, on the other hand, and the object being imaged onto at least one detector by means of an imaging optical arrangement, characterized in that the light serving for dark field illumination is pulsed, the pulse intensity of the light serving for dark field illumination being at least one order of magnitude greater than the intensity of continuous light serving for bright field illumination.

16. The method as claimed in claim 15, characterized in that the object inspection is carried out automatically.

17. The method as claimed in claim 15, characterized in that a device is coupled to a positioning system that positions the object, and in that object regions selected by means of the positioning system are automatically positioned in the inspection position.

* * * * *